US010638933B2

(12) United States Patent
Roukes (10) Patent No.: US 10,638,933 B2
(45) Date of Patent: May 5, 2020

(54) BRAIN-MACHINE INTERFACE BASED ON PHOTONIC NEURAL PROBE ARRAYS (71) Applicant: California Institute of Technology, Pasadena, CA (US)

(72) Inventor: Michael L. Roukes, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

(21) Appl. No.: 15/602,048

(22) Filed: May 22, 2017

(65) Prior Publication Data
US 2017/0347888 A1 Dec. 7, 2017

Related U.S. Application Data (63) Continuation of application No. 13/627,755, filed on Sep. 26, 2012, now abandoned.

(60) Provisional application No. 61/539,133, filed on Sep. 26, 2011, provisional application No. 61/568,331, filed on Dec. 8, 2011.

(51) Int. Cl.
A61B 5/00 (2006.01)

(52) U.S. Cl.
CPC .......... *A61B 5/0084* (2013.01); *A61B 5/4064* (2013.01); *A61B 5/6868* (2013.01); *A61B 2562/0233* (2013.01); *A61B 2562/046* (2013.01)

(58) Field of Classification Search
CPC ................ A61B 5/4064; A61B 5/6868; A61B 2562/0233
See application file for complete search history.

(56) References Cited

U.S. PATENT DOCUMENTS 5,195,161 A    3/1993  Adar et al.
5,807,261 A    9/1998  Benaron et al.
6,048,359 A *  4/2000  Biel .................... A61N 5/0601
                                                        606/2
(Continued)

FOREIGN PATENT DOCUMENTS

JP    2004-097590 A    4/2004
JP    2004-121702 A    4/2004
(Continued)

OTHER PUBLICATIONS

"Prosthetic systems for therapeutic optical activation and silencing of genetically targeted neurons" by J.G. Bernstein et al, Proc. SPIE 6854, Optical Interactions with Tissue and Cells XIX, 68540H pp. 1-11 (Feb. 12, 2008).*
(Continued)

*Primary Examiner* — Jeffrey G Hoekstra
*Assistant Examiner* — Jason M Ip
(74) *Attorney, Agent, or Firm* — Brooks Kushman P.C.

(57) ABSTRACT

Method and apparatus for illuminating and imaging tissue is provided. In one version, the method includes illuminating a volume of a tissue with photons from a three-dimensional array of optical emitters inserted into the tissue. In another version, the method includes detecting photons from a volume of a tissue using a three-dimensional array of optical detectors inserted into the tissue. A probe device for illuminating tissue and/or detecting photons emitted from tissue includes elongated microsized probes containing optical emitters and optical detectors in a three dimensional array.

19 Claims, 6 Drawing Sheets

(56) References Cited

U.S. PATENT DOCUMENTS

| | | |
|---|---|---|
| 6,485,413 B1 | 11/2002 | Boppart et al. |
| 6,528,802 B1 | 3/2003 | Koenig |
| 6,787,868 B1 | 9/2004 | McGreer |
| 6,819,858 B2 | 11/2004 | Steinberg et al. |
| 6,904,302 B2 | 6/2005 | Hirabayashi |
| 7,430,254 B1* | 9/2008 | Anderson ............... H04B 1/69 370/210 |
| 2002/0187533 A1* | 12/2002 | Mross .................... A61B 5/415 435/173.1 |
| 2004/0021100 A1* | 2/2004 | Gouzman ........... G01F 23/2927 250/573 |
| 2005/0141813 A1 | 6/2005 | Nakagawa |
| 2006/0129210 A1 | 6/2006 | Cantin |
| 2007/0293792 A1* | 12/2007 | Sliwa ...................... A61B 5/11 600/587 |
| 2009/0088680 A1* | 4/2009 | Aravanis ............. A61K 48/005 604/21 |
| 2009/0118800 A1 | 5/2009 | Deisseroth et al. |
| 2009/0210039 A1 | 8/2009 | Boyden |
| 2009/0326385 A1* | 12/2009 | Hendriks ............ A61B 5/0066 600/478 |
| 2011/0112591 A1* | 5/2011 | Seymour ............. A61B 5/0084 607/3 |
| 2011/0233046 A1 | 9/2011 | Nikolenko et al. |
| 2011/0295347 A1 | 12/2011 | Wells |
| 2012/0287420 A1 | 11/2012 | McLaughlin et al. |
| 2013/0085398 A1 | 4/2013 | Roukes |

FOREIGN PATENT DOCUMENTS

| | | |
|---|---|---|
| JP | 2006-112988 A | 4/2006 |
| JP | 2008-188123 A | 8/2008 |
| JP | 2010-511463 A | 4/2010 |
| KR | 10-2009-0044770 A | 5/2009 |
| WO | 2011-068696 A2 | 6/2011 |

OTHER PUBLICATIONS

Yizhar, O., et al., Optogenetics in Neural Systems. Neuron, 2011. 71.
Zhang, F., et al., Channelrhodopsin-2 and optical control of excitable cells. Nature Methods, 2006. 3(10).
Zhang, F., et al., Red-shifted optogenetic excitation: a tool for fast neural control derived from Volvox carteri. Nat Neurosci, 2008. 11(6).
Boyden, E., et al., Millisecond-timescale, genetically targeted optical control of neural activity. Nat Neurosci, 2005. 8(9).
Sineshchekov, O.A., K.-H. Jung, and J.L. Spudich, Two rhodopsins mediate phototaxis to low- and high-intensity light in Chlamydomonas reinhardtii. P Natl Acad Sci USA, 2002. 99(13).
Zhang, J., et al., Integrated device for optical stimulation and spatiotemporal electrical recording of neural activity in light-sensitized brain tissue. J Neural Eng, 2009. 6(5).
Zorzos, A., E. Boyden, and C. Fonstad, Multiwaveguide implantable probe for light delivery to sets of distributed brain targets. Optics Letters, 2010. 35(24).
Royer, S., et al., Multi-array silicon probes with integrated optical fibers: light-assisted perturbation and recording of local neural circuits in the behaving animal. Eur J Neurosci, 2010. 31(12).
Dakss, M., et al., Grating coupler for efficient excitation of optical guided waves in thin films. Appl Phys Lett, 1970. 16(12).
Henry, C.H., G.E. Blonder, and R.F. Kazarinov, Glass waveguides on silicon for hybrid optical packaging. Journal of Lightwave Technology, 1989. 7(10).
Melloni, A., et al., Ring-resonator filters in silicon oxynitride technology for dense wavelength-division multiplexing systems. Optics Letters, 2003. 28(17).
Brackett, C.A., Dense wavelength division multiplexing networks: principles and applications. IEEE Journal on Selected Areas in Communications, 1990. 8(6).
Smit, M. Progress in AWG design and technology. in Proceedings of 2005 IEEE/LEOS Workshop on Fibres and Optical Passive Components. 2005. IEEE.
M. K. Smit: "New focusing and dispersive planar component based on an optical phased array," Electron. Lett. 24, 385-386 (1988).
Takada, K., et al., 10-GHz-Spaced 1010-Channel Tandem AWG Filter Consisting of One Primary and Ten Secondary AWGs. IEEE Photonics Technology Letters, 2001. 13(6).
Smit, M. and C. van Dam, PHASAR-Based WDM-Devices: Principles, Design and Applications. IEEE Journal of Selected Topics in Quantum Electronics, 1996. 2(2).
Du, J., et al., High-Resolution Three-Dimensional Extracellular Recording of Neuronal Activity With Microfabricated Electrode Arrays. J Neurophysiol, 2008. 101.
Deshpande, S., et al., Optical properties of silicon nitride films deposited by hot filament chemical vapor deposition J Appl Phys, 1995. 77(12).
Haeiwa, H., T. Naganawa, and Y. Kokubun, Wide Range Center Wavelength Trimming of Vertically Coupled Microring Resonator Filter by Direct UV Irradiation to SiN Ring Core. IEEE Photonics Technology Letters, 2004. 16(1).
Wang, T.-J., Y.-H. Huang, and H.-L. Chen, Resonant-Wavelength Tuning of Microring Filters by Oxygen Plasma Treatment. IEEE Photonics Technology Letters, 2005. 17(3).
Loeb, G., et al., Paryelen as a chronically stable, reproducable microelectrode insulator. IEEE Trans. Biomed. Eng., 1977. 24(2).
Duncan, W.M., et al., The DLP™ Switched Blaze Grating: The Heart of Optical Signal Processing. SPIE Proceedings, 2003. 4983.
Dudley, D., W. Duncan, and J. Slaughter, Emerging Digital Micromirror Device (DMD) Applications. SPIE Proceedings, 2003. 4985.
Maire, G., et al., High efficiency silicon nitride surface grating couplers Optics Express, 2007. 16(1).
Doerr, C.R., et al., Wide Bandwidth Silicon Nitride Grating Coupler. IEEE Photonics Technology Letters, 2010. 22(19).
Okamoto, K. and A. Sugita, Flat spectral response arrayed-waveguide grating multiplexer with parabolic waveguide horns. Electronics Letters, 1996. 32(18).
Cheben P., et al., A high-resolution silicon-on-insulator arrayed waveguide grating microspectrometer with sub-micrometer aperture waveguides. Optics Express, 2007. 15(5).
A. H. Buist, et al., "Real time two-photon absorption microscopy using multi point excitation", Journal of Microscopy, vol. 192, Pt 2, Nov. 1998, pp. 217-226.
Bernstein, J. G et al., "Prosthetic systems for therapeutic optical activation and silencing of genetically targeted neurons" Proc. SPIE 6854, Optical Interactions with Tissue and Cells XIX, 68540H pp. 1-11 (Feb. 12, 2008).
PCT Search Report dated Feb. 8, 2013 in connection with related PCT Patent Application No. PCT/US2012/057332.

\* cited by examiner

BRAIN-MACHINE INTERFACE BASED ON PHOTONIC NEURAL PROBE ARRAYS

CROSS-REFERENCE TO RELATED APPLICATIONS

This application is a continuation of prior application Ser. No. 13/627,755, filed on Sep. 26, 2012, which claims the benefit of Provisional Patent Application Nos. 61/539,133, filed on Sep. 26, 2011, and 61/568,331, filed on Dec. 8, 2011, all of which are incorporated by reference herein.

BACKGROUND

Field of the Invention

The invention relates to an apparatus and method for illuminating and imaging tissue.

Related Art

In the past decade, there has been an interest in stimulating neurons using light-activated ion channels (Yizhar, O., et al., Optogenetics in Neural Systems, 2011, Neuron 71; Zhang, F., et al., Red-shifted optogenetic excitation: a tool for fast neural control derived from Volvox carteri., 2008, Nat. Neurosci. 11(6)). Light-activated channels allow for light-activated modulation of neuron membrane potentials, and light-activated channels can be delivered to individual neuron types for specific activation of target neurons. The most effective stimulatory protein to date is channelrhodopsin-2 (Yizhar, O., et al., Optogenetics in Neural Systems, Neuron 71, 2011; Zhang, F., et al., Channelrhodopsin-2 and optical control of excitable cells, 2006, Nature Methods 3(10); Boyden, E., et al., Millisecond-timescale, genetically targeted optical control of neural activity, 2005, Nat. Neurosci 8(9)). Channelrhodopsin-2 is a light-stimulated cation channel from the green algae *C. reinhardtii* (Sineshchekow, O. A., et al., Two rhodopsins mediate phototaxis to low- and high-intensity light in *Chlamydomonas reinhardtii*, 2002, Proc. Natl. Acad. Sci. (USA) 99(13)), and can be used to stimulate neurons optically (Boyden, E., et al., Millisecond-timescale, genetically targeted optical control of neural activity, 2005, Nat. Neurosci 8(9)). There are now different proteins available for optogenetic excitation or inhibition of neurons (Yizhar, O., et al., Optogenetics in Neural Systems, 2011, Neuron 71).

Neural probes for stimulation of light-activated channels are desirable, although current technology involves crude approaches such as simply gluing an optical fiber directly to a neural shank (Royer, S., et al., Multi-array silicon probes with integrated optical fibers: light-assisted perturbation and recording of local neural circuits in the behaving animal, 2010, Eur. J. Neurosci. 31(12)). Another neural probe has been described having twelve optical waveguides fabricated on a simple silicon oxynitride shank (Zorzos, et al., Multi-waveguide implantable probe for light delivery to sets of distributed brain targets, 2010, Optics Letters 35(24)).

SUMMARY

The inventors recognize that an optically-based system capable of providing dense local interactions with large numbers of neurons in living tissue is desirable.

In one aspect, a first method for examining a tissue is provided. The method includes illuminating a volume of a tissue with photons from a three-dimensional array of optical emitters inserted into the tissue. The tissue can be neural tissue, which in some embodiments is brain tissue. In some embodiments, the tissue, including neural tissue, can be prepared by optogenetic methods. The array in any embodiment can include elongated microsized probes that contain the optical emitters. Also, the source of the photons can comprise an emission multiplexer.

The illuminating can result in neurostimulation of the tissue. In some embodiments, the illuminating results in stimulation of chemical reporter molecules in the tissue, in stimulation of voltage reporting molecules in the tissue, in stimulation of stress- or mechano-reporting molecules in the tissue, or a combination thereof.

In the method, the optical resolution of the array can be about 200 µm in at least one dimension of the volume. In addition, the illuminating can include two-photon or multiple photon excitation of the volume.

In another aspect, a second method for examining a tissue is provided. The method includes detecting photons from a volume of a tissue using a three-dimensional array of optical detectors inserted into the tissue. The tissue can be neural tissue, which in some embodiments is brain tissue. In some embodiments, the tissue, including neural tissue, can be prepared by optogenetic methods. The array in any embodiment can include elongated microsized probes that contain the optical detectors. In some embodiments, the photons are produced by illuminating the tissue volume.

The photons in some embodiments can be emitted from chemical reporter molecules in the tissue, from voltage reporting molecules in the tissue, from stress- or mechano-reporting molecules in the tissue, or a combination thereof.

In the method, the optical resolution of the array can be about 200 µm in at least one dimension of the volume. In addition, the photons can be produced by two-photon or multiple photon excitation of the volume. Also, the photons can be produced by illuminating the tissue volume using a three-dimensional array of optical emitters inserted into the tissue. Thus, the first method involving illuminating and the second method involving detecting can be combined into a single method.

In a further aspect, a device for examining a tissue is provided. The device can be used for practicing the methods described herein. The device includes elongated microsized probes, each probe comprising one or more optical emitters, or one or more optical detectors, or both one or more optical emitters and one or more optical detectors. In the device, the probes are arranged to form a three-dimensional array of the one or more optical emitters or a three-dimensional array of the one or more optical detectors, or both a three-dimensional array of the one or more optical emitters and a three-dimensional array of the one or more optical detectors. In some embodiments, the probes have cross-sectional diameters of about 10 µm or less. In some embodiments, the probes are of a size so as not to cause gliosis. The one or more optical emitters and/or one or more optical detectors in any embodiment can be arranged along the length of the probes. The device can further include one or more optical sources optically connected to the probes. The one or more optical sources can comprise an emission multiplexer.

In some embodiments, the one or more optical emitters are waveguide terminals. In some embodiments, the one or more optical emitters are optical devices, which in some embodiments can be micro-ring resonators, photonic crystal resonators, nanobeam cavities, diffraction gratings, waveguide-coupled gratings, or etched, chip-integrated 45-degree mirrors, or a combination thereof. In some embodiments, the one or more optical emitters is any combination of the optical devices and waveguide terminals. In some embodiments, the one or more optical detectors can be Si photodetectors, Ge photodetectors, grating-coupled detectors, or a combination thereof. Any combination of these optical emitters and optical detectors is contemplated.

In the device, the optical resolution of the array of emitters and/or the array of detectors can be about 200 μm.

In another aspect, a system comprising the device and further comprising one or more optical sources optically connected to the probes is provided. The one or more optical sources can comprise an emission multiplexer.

BRIEF DESCRIPTION OF THE DRAWINGS

For a more complete understanding of the present invention, reference is now made to the following descriptions taken in conjunction with the accompanying drawings, in which.

DETAILED DESCRIPTION

In a particular aspect, an optically based system capable of providing dense local interactions with large numbers of neurons or other cell types in living tissue is provided. The implementation is multifunctional and amongst its potential applications are: high-resolution local imaging of large volumes of neural or other tissue, recording the extracellular and intracellular potentials of large numbers of neurons within such volumes, and highly selective local stimulation of neurons based on optogenetic excitation.

The system can comprise a large array of elongated probes (such as neural probes) with small cross-section, each studded with its own three dimensional (3D) array of optical emitters or optical detectors, or both optical emitters and detectors. Preserving a narrow cross-section maximizes the capability of the probes to be used for chronic applications in neural tissue without attendant gliosis. Taken together, the ensemble constitutes separate arrays of optical emitters and/or optical detectors that densely fill a volume of neural or other tissue. The desired density of the 3D array can be set by the fundamental length scale over which the interactions (e.g. 2-photon excitation, etc.) decay.

The optical emitters can be employed for one-photon, two-photon, or multiple photon excitation of both nanoparticles, dyes, molecules, or other entities. This excitation can enable both neurostimulation and optical imaging that is highly local and selective.

The three-dimensional array of optical detectors can permit ultrafast, highly-oversampled reconstruction of optical emission from neural or other tissue (appropriately labeled, as necessary, with local reporters, dyes, etc.) resulting from selective local excitation. Given that the optical excitation and detection elements can be readily configured to provide sampling at the picosecond scale or faster, temporal resolution of local spiking of neurons or tracking of intracellular potential can be achieved with use appropriate local-potential-sensing nanoparticles, dyes, molecules, or other entities that yield adequate voltage sensitivity.

Figure 1:
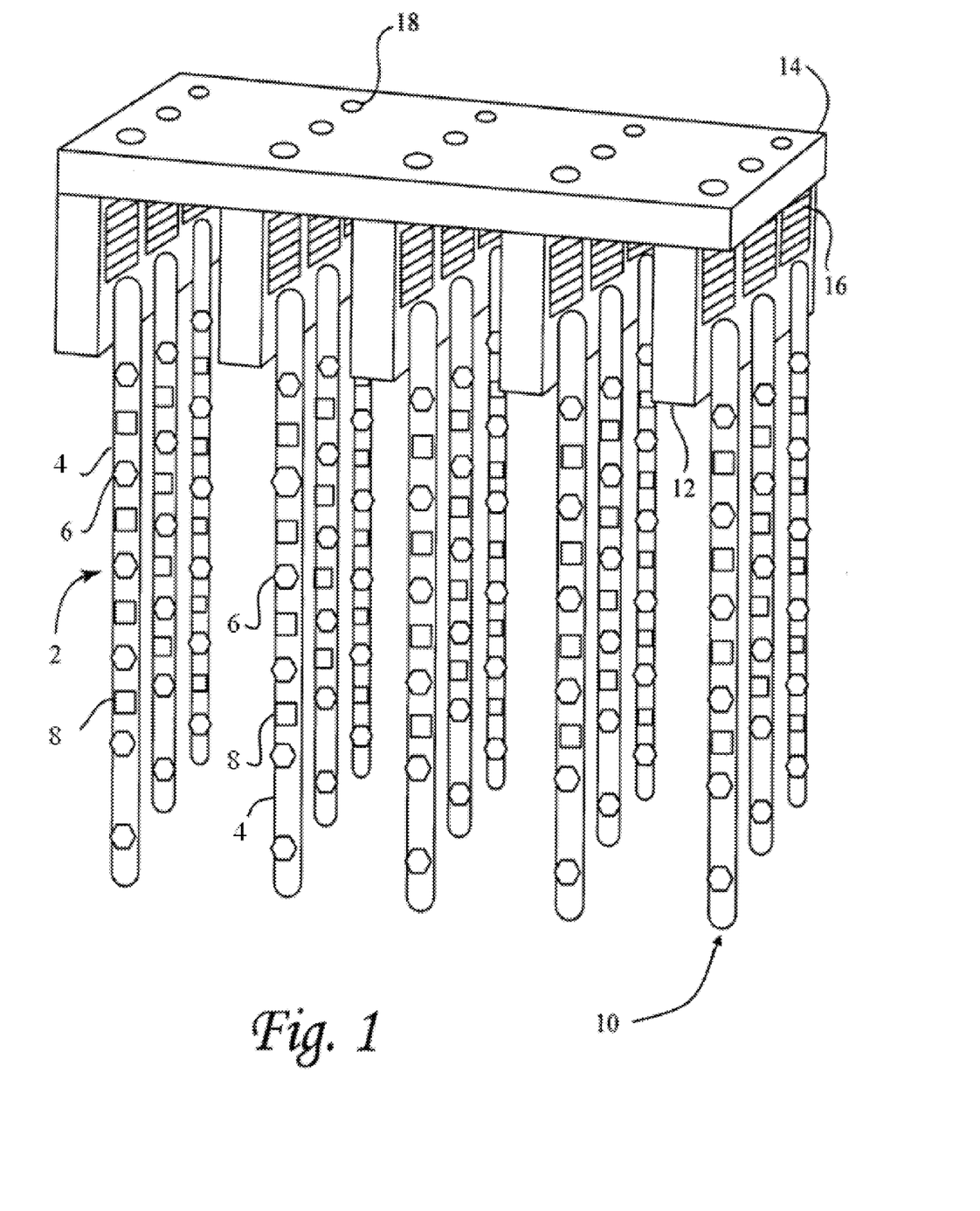
FIG. 1 is a schematic drawing of an embodiment of a probe device.

Referring to FIG. 1, one embodiment of a probe device includes an elongated probe 2 containing a probe shank 4, an optical emitter 6 and an optical detector 8. In the embodiment, planar, two dimensional arrays of probe shanks are provided, each array 10 attached to a separate probe body 12, which can be a single-shank or multi-shank probe body. A plurality of multi-shank probe bodies are themselves aligned within a probe headstage 14 to form a three dimensional array of probes. On each of the multi-shank probe bodies, one or more than one grating coupler 16 allows efficient coupling between optical fibers from an optical source, such as an emission multiplexer, and integrated optical waveguides that are on each of the probe shanks.

The embodiment depicted in FIG. 1 is based on a micromechanical assembly of locking shank probe bodies into an appropriately configured probe headstage. Optical fibers (waveguides) from an optical source such as an emission multiplexer can be similarly mechanically attached at one or more than one attachment point 18 to the grating couplers for each probe shank. Other probe assemblies can employ full 3D integration, which will permit mechanical assemblies to be circumvented entirely. This integrated approach will employ optical excitation elements—sources that might include, but are not limited to, surface-emitting or edge-emitting laser diodes, or light-emitting diodes—to be co-fabricated with the optical waveguides themselves, on-chip. A significant benefit of full three-dimensional integration is that the pitch between the probe bodies (the two dimensional entities from which the full three dimensional architecture is constructed) can be significantly smaller than what can be achieved by mechanical assembly. In the case of 3D integration, the probe body-to-probe body pitch is limited only by the requisite layer thickness of the probe bodies themselves.

A three-dimensional array of emitters can be sequentially excited by a combined spatial-and-wavelength-addressing (SAWA) method. One embodiment of an emission multiplexer is the SAWA system pictured in FIG. 2, in which a controller 20 directs a frequency shift driver 22 and a raster driver 24, both connected to a first and a second laser 26,28, respectively. In this configuration, a plurality of optical beams, such as one beam 30 from the first laser and another beam 32 from the second laser, can be utilized. The optical beams are optically connected to one or more than one optical waveguide 34, which alone or with other optical waveguides forms a fiber matrix 36. A fiber matrix termination block 38 organizes the fiber matrixes, with one end of each fiber matrix terminating at a fiber termination 40 in the block. An optical coupler is present at each fiber termination for optical connection to one or both optical beams. The other end of a fiber matrix can be connected to a probe device, for example, at the attachment point 18 of the device shown in FIG. 1.

Figure 2:
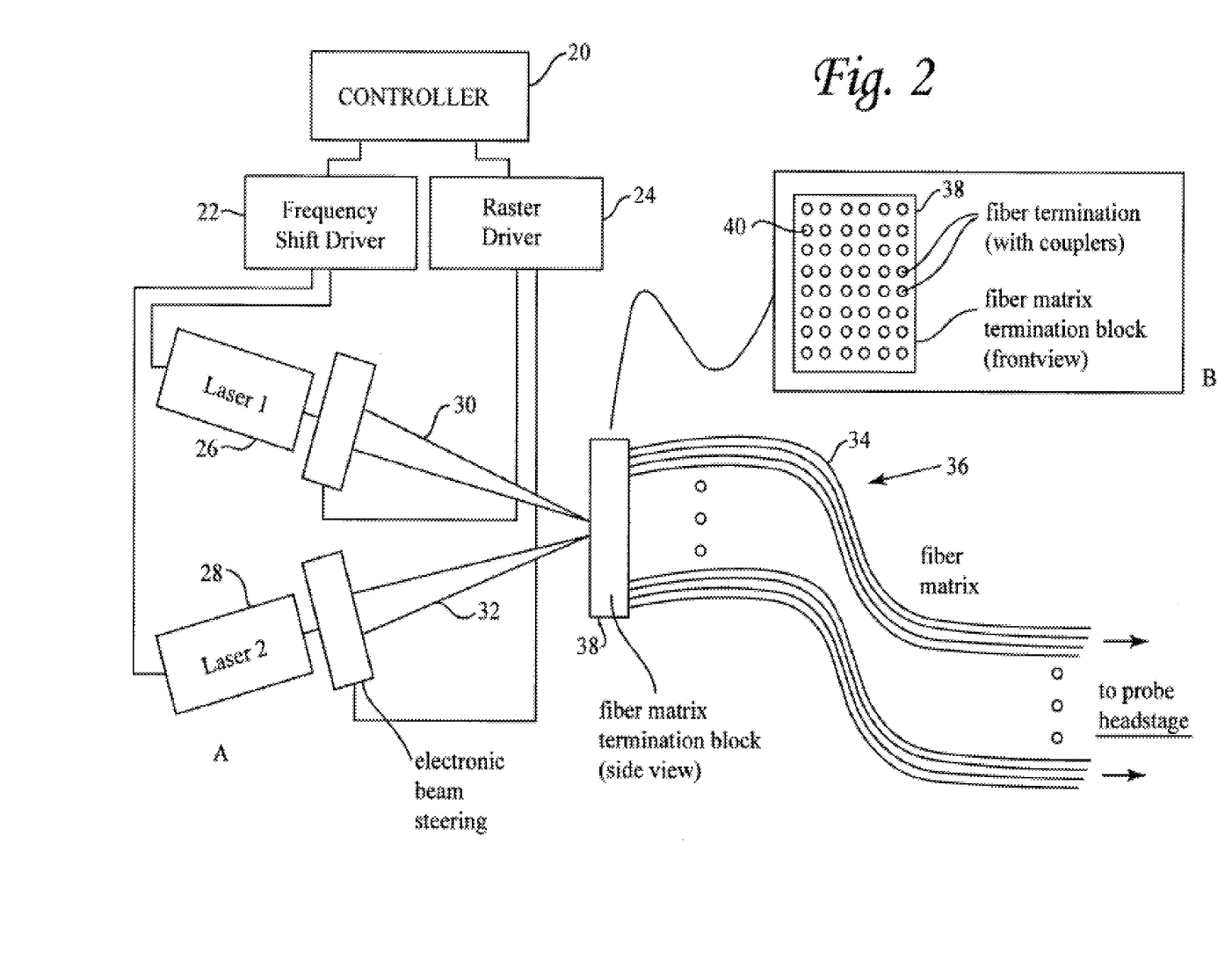
FIG. 2 is a schematic drawing of an embodiment of an emission multiplexer. In (A), an automated fiber addressing/excitation system emission multiplexer is shown, with a side view of a termination block depicted; in (B), a front view of the termination block is shown.

Referring to FIG. 2, the optical beams can be simultaneously both spatially rastered and wavelength shifted to enable a temporally coherent, programming protocol. This combination of programming enables addressing both the individual optical waveguides (which can be directly coupled to individual probes, such as the probes shown in FIG. 1), as well as the individual emitter elements from amongst the array on each of the probes (which can be wavelength addressable by resonant optical elements).

Other embodiments of SAWA implementations can use full 3D integration, which can enable realization of multiplexing without the mechanical assemblies and free-space optical propagation depicted in FIG. 2. For example, coupling pairs of integrated optical sources to each optical fiber or waveguide would allow the individual SAWA "channels" to be electronically activated (addressed). Such sources can include, but are not limited to, surface-emitting or edge-emitting laser diodes, light-emitting diodes, and the like.

Figure 3:
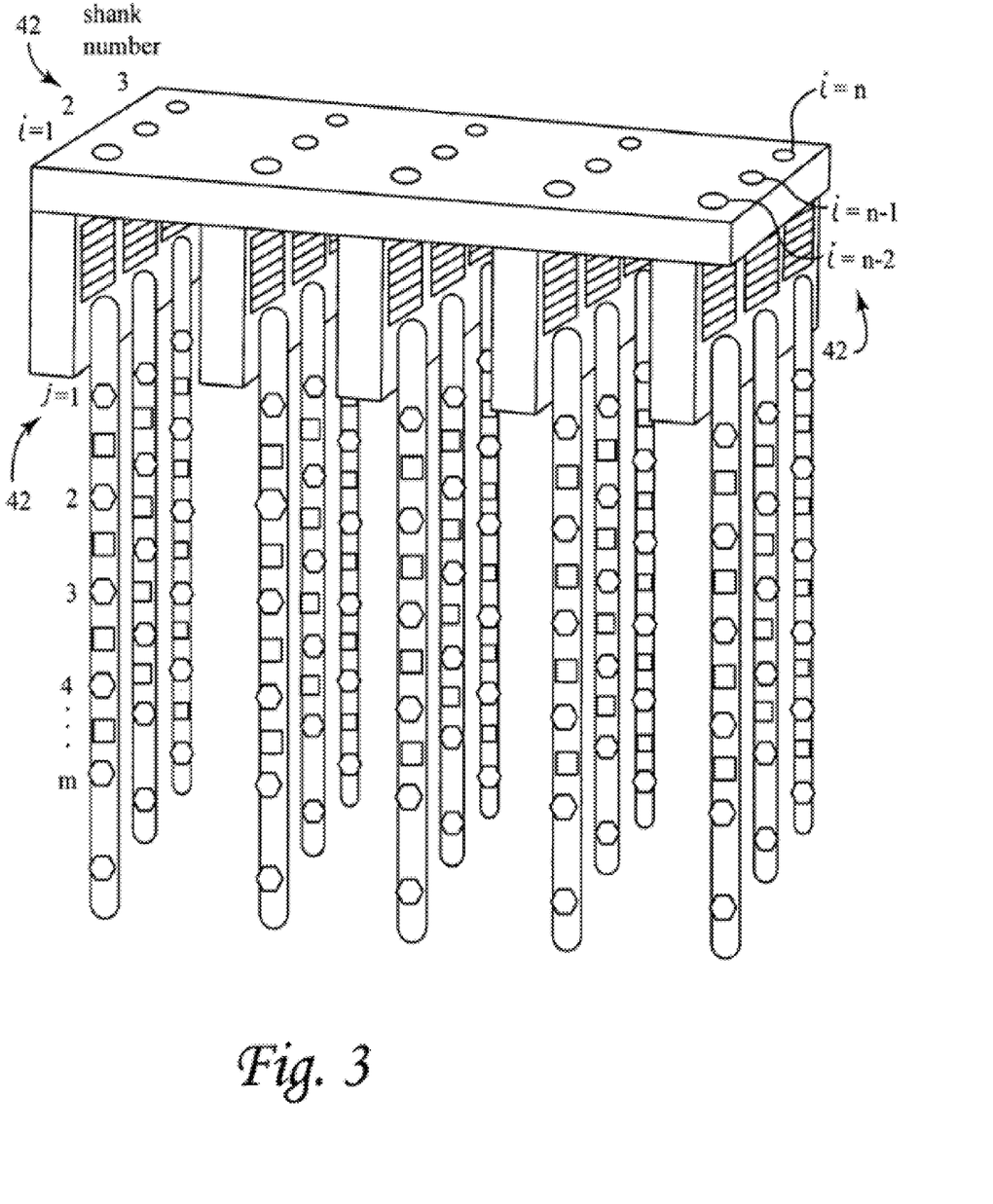
FIG. 3 is a schematic drawing of an embodiment of a pixel addressing system for a three-dimensional emission and/or detector pixel array.

A numbering system 42 can be used to describe a three-dimensional emission pixel array, as shown in FIG. 3. A similar scheme can be used to number a detector pixel array. Individual probe shanks can be labeled with index i, whereas the individual emitter pixels (or detector pixels) on a given shank can be labeled with index j(k).

Referring to the embodiment in FIG. 1, each probe shank can be studded with its own separate array of one or more than one optical emitter 6 and/or optical detector 8. The probe-specific emitter arrays can be (i) coupled as an ensemble to a common optical bus, or (ii) each emitter element can be coupled to its own probe-integrated optical waveguide. In the first case, a single optical waveguide running longitudinally down each probe shank can be evanescently-coupled to the probe-specific array of optical emitters. Each emitter in this first case would be coupled to the common bus resonantly, at an emitter-pixel-specific wavelength in a fashion akin to wavelength division multiplexing. In the second case, each probe shank would contain a plurality of integrated optical waveguides running longitudinally down its length; each of these waveguides would terminate in (i.e. be specifically coupled to) its own optical emitter.

The term "optical emitter" refers to an optical element from which light and other optical radiation is emitted. Depending on the particular embodiment and configuration of a probe device, the optical emitter can be, for example, a waveguide terminal or can be an optical element such as a micro-ring resonator, a photonic crystal resonator, or a microfabricated diffraction grating. The term "emitter pixel" refers to the point on a probe where light is emitted.

Figure 4:
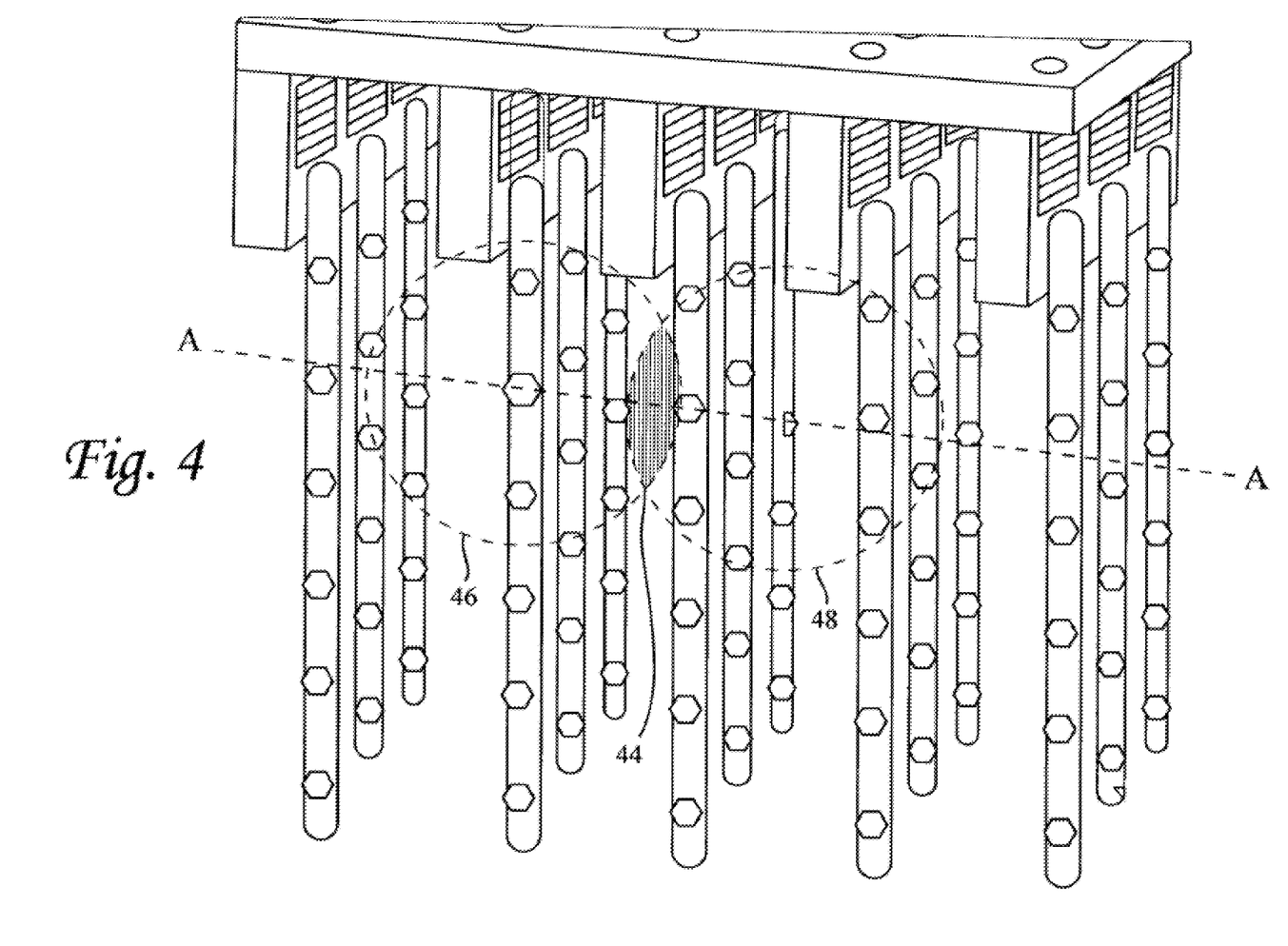
FIG. 4 is a schematic drawing of two active emitters and a resulting volume of 2-photon excitation.

One-, two-, or multiple photon methods of illumination can be achieved by appropriate programming of an emitter-pixel excitation protocol. FIG. 4 makes apparent that the entire volume of neural tissue spanned by the emitter pixel array can be covered in a piece-wise continuous, but highly-local, manner by addressing pairs of emitter pixels to which the excitation is sequentially applied. Stepping through the sequence of pairs in the array illuminates overlapping "slices" of the neural tissue. In other excitation protocols, different groups of emitter pixels can be addressed to provide alternate patterns of illumination.

FIG. 4 illustrates the effective volume 44 of 2-photon excitation for one specific step of a time-stepped protocol, in which a sequential ensemble of temporally-programmed emitter pairs are excited. For the specific step of the sequence that is illustrated, the effective volume illuminated is localized on a plane perpendicular to a longitudinal axis A spanning the two active emitters for this specific step of the temporal sequence. The illuminated volume 46 for one member of the emitter pair, and the illuminated volume 48 for the other member of the emitter pair are also shown in the figure. In some embodiments, the optical resolution of an emitter array is about 200 µm in at least one dimension of the volume illuminated. Thus, the array can sample about a 200 µm portion of a tissue.

Figure 5:
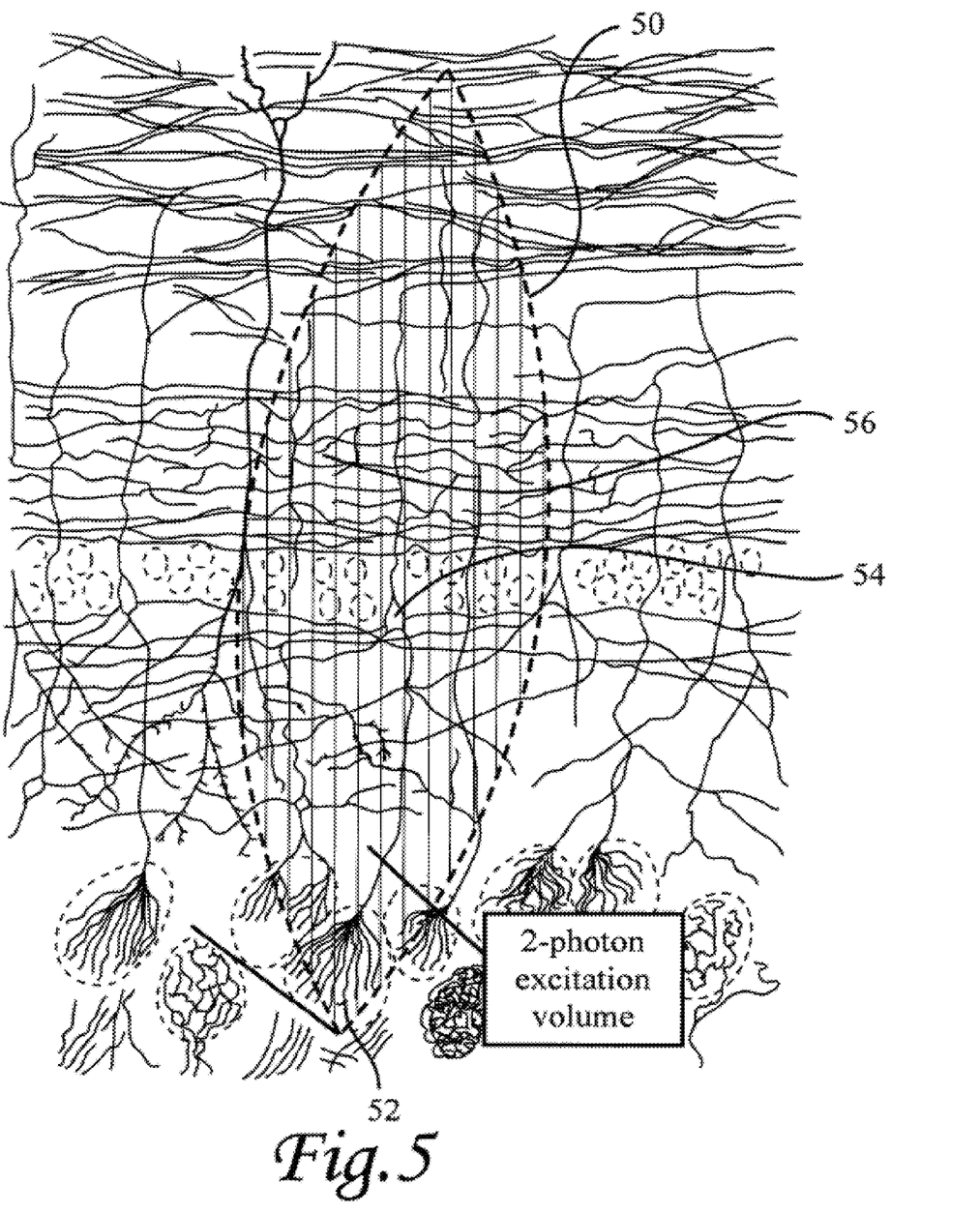
FIG. 5 is a schematic drawing of a 2-photon excitation volume of illuminated neural tissue.

FIG. 5 shows a conceptual view of a two-photon excitation volume 50 illuminating a neural tissue. Some possible targets for two-photon optical excitation include, but are not limited to, a specifically labeled dendrite 52, specifically-labeled cell body 54, synaptic junction 56 or synaptic cleft, specifically labeled interior component within neural cells such as a synaptic vesicle, and the cell membrane itself. When probes are localized within the cell membrane, use of an electric- or magnetic-field sensitive optical probe would permit optical resolution of the intracellular potential of the labeled neuron. A complementary modality would involve use of electric- or magnetic-field dependent probes in the extracellular medium; in this case the extracellular potential (and neural spiking) would be sensed.

Figure 6:
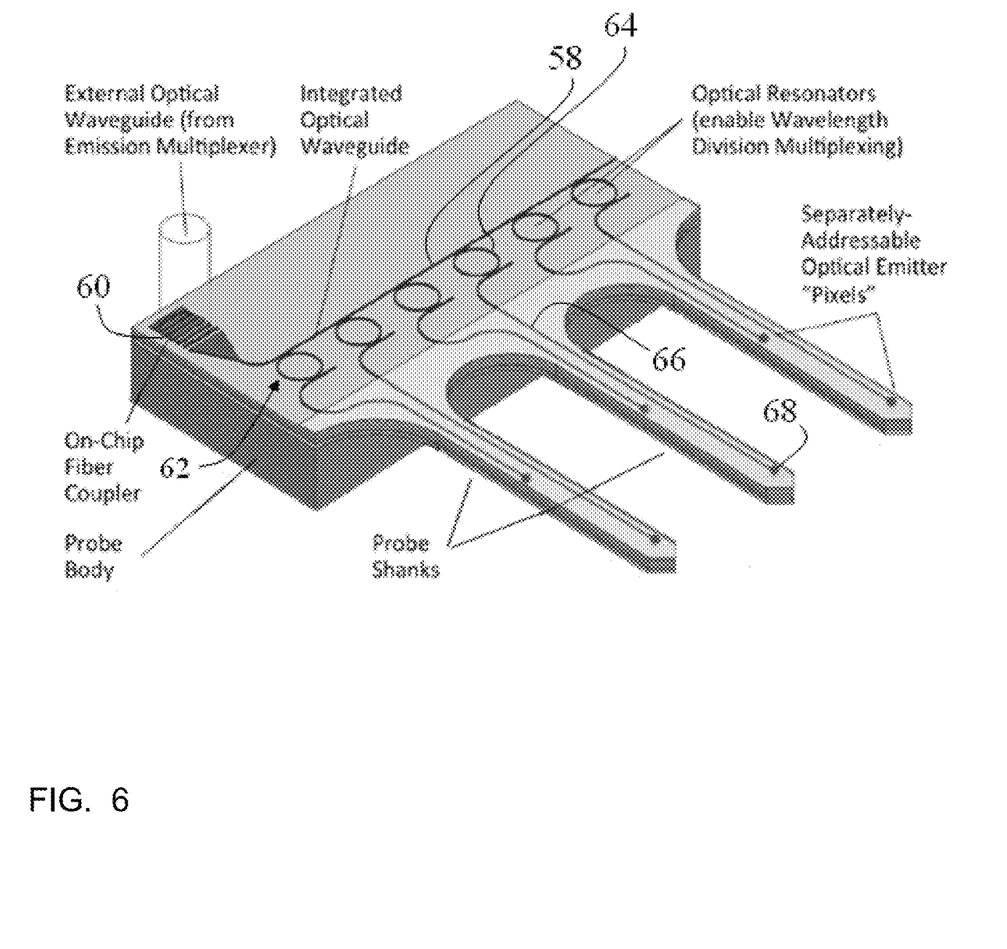
FIG. 6 is a schematic drawing of a neural probe.

FIG. 6 shows a way of preparing a neural probe having a common optical bus. In this embodiment, an optical input can be coupled to a bus waveguide 58 using a grating coupler 60 leading to a ring resonator array 62. Each ring resonator 64 is evanescently coupled to the bus waveguide 58 and a terminal waveguide 66, providing for power transfer into the terminal waveguide. Light emerges from the end of the terminal waveguide at an optical emitter pixel 68.

In other embodiments, resonant addressing of individual emitter pixels can also occur via micro-ring resonators, photonic crystal resonators, microfabricated diffraction gratings, or waveguide terminated grating couplers, or use of simple out-of-plane reflecting elements, incorporated into and along a probe shaft. The examples listed above are meant to be illustrative, but not exhaustive.

Separate arrays of optical detectors (or detection pixels), integrated onto each probe shank, permit acquisition of spatially-dense and highly oversampled data from optical emissions within the tissue surrounding the entire probe array. This can provide the basis for highly local reconstruction of optical emission within the sampled volume, with very high spatial resolution. Detection pixels can be differentiated into categories of active local detection, and passive local collection. Possible implementations of the active local detection pixels include use of electro-optic elements such as Si and Ge photodetectors, among a range of possibilities. Connection to each of these active detection elements would be enabled by separate electrical waveguides running longitudinally along the probe shafts. Possible implementations of detection pixels utilizing passive local collection could employ grating-coupled collectors at the terminus of separate optical waveguides that run longitudinally along the shaft to subsequent active optical detection elements (located elsewhere, such as on the probe body, on the probe headstage, or beyond.) The optical acceptance angle of such grating couplers can be extended by use of local microfabricated lenses placed optimally above each grating.

A probe device can include both optical emitters and optical detectors. Such devices can be used to both illuminate and detect photons. In other embodiments, a probe device can include only optical emitters. In this case, the probe device can be used to illuminate tissue. Alternatively, a probe device can include only optical detectors, and can be used to detect photons.

Although the system has been described mainly in connection with neural tissue, the methods, systems, devices and other embodiments are also applicable to other tissues, such as muscle. Examples of cells in that can be investigated and appropriately labeled include, but are not limited to, neurons, glial cells and muscle cells. The tissue can be in an organism, or can be explanted tissue.

In some embodiments, the tissue can be prepared by optogenetic methods. In optogenetics, photoactivatable proteins, receptors or channels can be incorporated into tissues, making the tissues photo-responsive (Yizhar, O., et al., Optogenetics in Neural Systems, Neuron 71, 2011; Zhang, F., et al., Channelrhodopsin-2 and optical control of excitable cells, Nature Methods 3(10), 2006; Boyden, E., et al., Millisecond-timescale, genetically targeted optical control of neural activity, Nat. Neurosci 8(9), 2005).

A probe can be sized to be used in neural tissue without causing gliosis by, for example, keeping the volume of the probe much less than the volume of a neural cell. For example, a microsized probe has a cross-sectional diameter in the range of about 10 µm to about 50 µm, or about 10 µm to about 25 µm. In some embodiments, a microsized probe can have a cross-sectional diameter of about 10 µm or less. The density of probes on a probe device can be configured to minimize gliosis or tissue damage.

The photons emitted from a tissue and detected by a probe device can be produced by photoluminescence, chemiluminescence, bioluminescence, or other types of luminescence, or combinations thereof. For example, a tissue labeled with a dye can emit photons by photoluminescence, which can be detected by the probe device. Also, a tissue labeled with a potential-sensing nanoparticle can emit photons when the tissue potential changes; the emitted photons can then be detected by the probe device. Stimulation of a tissue to emit photons can be accomplished by electrical stimulation, chemical or biological stimulation, illumination, or other means. For example, neural tissue labeled with a potential-sensing nanoparticle could be electrically stimulated or treated with a neural transmitter to stimulate tissue potential changes for detection by the probe device. Illumination of tissue by a probe device, as described herein, can also lead to stimulation of chemical reporter molecules in the tissue, or stimulation of stress- and mechano-reporting molecules.

Although various components of the probe device have been described separately, it should be understood that any embodiment of one component is contemplated to be combined with any embodiment of another component. Thus, for example, any combination of optical emitters, optical detectors, fiber shanks and optical sources is envisioned. Similarly, although various features of the methods have been described separately, it should be understood that any embodiment of one feature is contemplated to be combined with any embodiment of another feature.

REFERENCES

The following publications are incorporated by reference herein:

Yizhar, O., et al., Optogenetics in Neural Systems, 2011, Neuron 71, 9-34.
Zhang, F., et al., Red-shifted optogenetic excitation: a tool for fast neural control derived from Volvox carteri., 2008, Nat. Neurosci. 11(6), 631-633.
Zhang, F., et al., Channelrhodopsin-2 and optical control of excitable cells, Nature Methods, 2006, 3(10), 785-792.
Boyden, E., et al., Millisecond-timescale, genetically targeted optical control of neural activity, 2005, Nat. Neurosci 8(9), 1263-1268.
Sineshchekow, O. A., et al., Two rhodopsins mediate phototaxis to low- and high-intensity light in *Chlamydomonas reinhardtii*, 2002, Proc. Natl. Acad. Sci. (USA) 99(13), 8689-8694.
Royer, S., et al., Multi-array silicon probes with integrated optical fibers: light-assisted perturbation and recording of local neural circuits in the behaving animal, 2010, Eur. J. Neurosci. 31(12), 2279-2291.
Zorzos, et al., Multiwaveguide implantable probe for light delivery to sets of distributed brain targets, 2010, Optics Letters 35(24), 4133-4135.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the invention and the following claims.

What is claimed is:

1. A method for examining a tissue, comprising illuminating a volume of a tissue with optical beams of photons from a three-dimensional array of optical emitters inserted into the tissue wherein the optical emitters comprise waveguides terminated in an emitter element or elements having a cross-sectional diameter of about 10 µm to about 50 µm and wherein optical beams that excite the three-dimensional array of optical emitters are simultaneously both spatially rastered and wavelength shifted by a combined spatial- and -wavelength-addressing system.

2. The method of claim 1, wherein the tissue is a neural tissue.

3. The method of claim 2, wherein the neural tissue is prepared by optogenetic methods.

4. The method of claim 1, wherein the array comprises elongated microsized probes comprising the optical emitters.

5. The method of claim 1, wherein the optical resolution of the array permits oversampled reconstruction of optical emission from neural or other tissue.

6. The method of claim 1, wherein the photons are produced from a source that comprises an emission multiplexer.

7. The method of claim 1 wherein said photons are detected using a three-dimensional array of optical detectors inserted into the tissue wherein the optical detectors are one or more Si photodetectors, or grating-coupled detectors, a Ge photodetector, or a combination thereof.

8. The method of claim 7, wherein the tissue is a neural tissue.

9. The method of claim 7, wherein the array comprises elongated microsized probes comprising the optical detectors.

10. The method of claim 2, wherein the optical resolution of the array permits oversampled reconstruction of optical emission from said neural or other tissue.

11. A device for examining a tissue, comprising elongated microsized probes, each probe comprising a plurality of optical emitters and a plurality of optical detectors, wherein the probes are arranged to form a three-dimensional array of the plurality of optical emitters and/or a three-dimensional array of the plurality of optical detectors, and further wherein the optical emitters comprise waveguides terminated in an emitter element or elements having a cross-sectional diameter of about 10 µm to about 50 µm, and the optical detectors are a plurality of Si photodetectors, or grating-coupled detectors, or a combination thereof or each emitter, or a Ge photodetector or combination thereof and wherein the plurality optical emitters and the plurality of optical detectors are alternatingly arranged along the length of the probes.

12. The device of claim 11, further comprising one or more optical sources optically connected to the probes.

13. The device of claim 12, wherein the one or more optical sources comprise an emission multiplexer.

14. The device of claim 11 wherein there are a plurality of optical emitters and a plurality of optical detectors both arranged along the length of each of a plurality of the probes.

15. The method of claim 1 wherein the three-dimensional array is applied as a three-dimensional emission pixel array individual probe shanks, individual emitter pixels, and individual detector pixels are numbered with an index.

16. The method of claim 1 wherein the three-dimensional array includes a plurality of probe shanks with each probe shank studded with its own separate array of optical emitters optical detectors coupled a common optical bus.

17. The method of claim 16 wherein each emitter element is coupled to its own probe-integrated optical waveguide with a single optical waveguide running longitudinally down each probe shank that is evanescently-coupled to a probe-specific array of optical emitters with each emitter coupled to the common bus resonantly, at an emitter-pixel-specific wavelength.

18. The method of claim 16 wherein each probe shank includes a plurality of integrated optical waveguides running longitudinally down its length, waveguides terminating in an optical emitter.

19. The method of claim 16 further comprising addressing pairs of emitter pixels to which an excitation is sequentially applied and stepping through a sequence of pairs in the array to illuminates overlapping slices of the neural tissue.

\* \* \* \* \*